US012343247B2

(12) United States Patent
Chandrashekar

(10) Patent No.: US 12,343,247 B2
(45) Date of Patent: Jul. 1, 2025

(54) PROSTHETIC CARDIAC IMPLANT

(71) Applicant: Chandramouli Honnavalli Chandrashekar, Bangalore (IN)

(72) Inventor: Chandramouli Honnavalli Chandrashekar, Bangalore (IN)

( * ) Notice: Subject to any disclaimer, the term of this patent is extended or adjusted under 35 U.S.C. 154(b) by 1163 days.

(21) Appl. No.: 17/271,612

(22) PCT Filed: Aug. 29, 2019

(86) PCT No.: PCT/IB2019/057274
§ 371 (c)(1),
(2) Date: Feb. 26, 2021

(87) PCT Pub. No.: WO2020/250027
PCT Pub. Date: Dec. 17, 2020

(65) Prior Publication Data
US 2021/0338409 A1    Nov. 4, 2021

(30) Foreign Application Priority Data
Jun. 14, 2019   (IN) .............................. 201941023559

(51) Int. Cl.
*A61M 60/35* (2021.01)
*A61F 2/06* (2013.01)
*A61M 60/38* (2021.01)
*A61B 17/00* (2006.01)

(52) U.S. Cl.
CPC .............. *A61F 2/06* (2013.01); *A61M 60/35* (2021.01); *A61M 60/38* (2021.01); *A61B 2017/00252* (2013.01); *A61F 2002/061* (2013.01); *A61F 2002/068* (2013.01); *A61F 2220/0075* (2013.01); *A61F 2230/0067* (2013.01); *A61F 2230/0086* (2013.01); *A61F 2250/0039* (2013.01)

(58) Field of Classification Search
CPC ..................................... A61M 60/35
See application file for complete search history.

(56) References Cited

U.S. PATENT DOCUMENTS

2014/0336446 A1* 11/2014 Rodefeld ............ A61M 60/148
600/16

FOREIGN PATENT DOCUMENTS

WO    WO 2005/020848 A2 *  3/2005  .......... A61M 60/135

* cited by examiner

*Primary Examiner* — David H Willse

(57) ABSTRACT

The device (300) for use in total cavopulmonary connection comprises a hollow body (302), embedded within the cavity of which is a flow separator (308). The hollow body (302) comprises a first end (304) that is configured to receive blood from inferior vena cava (IVC) and a second end (306) configured to be connected to pulmonary artery. Further, the flow separator (308) aids in guiding blood from IVC and superior vena cava (SVC) to right pulmonary artery and left pulmonary artery. The flow separator (308) comprises an inferior end (402) and a superior end (404). The inferior end (402) is located between the first end (304) and the second end (306) of the hollow body (302). The flow separator (308) is dimensioned to have the superior end (404) enter SVC when the second end (306) is connected to the pulmonary artery.

19 Claims, 15 Drawing Sheets

PROSTHETIC CARDIAC IMPLANT

BACKGROUND

Unless otherwise indicated herein, the materials described in this section are not prior art to the claims in this application and are not admitted to being prior art by inclusion in this section.

FIELD OF INVENTION

The disclosed subject matter generally relates to the field of medical devices, and more particularly but not exclusively, to the field of artificial heart implants.

DISCUSSION OF PRIOR ART

Congenital heart disease (CHD) is defined as a problem in the heart's structure and function that is present at birth. It is reported that CHDs are the leading cause of infant morbidity and mortality. It is estimated that about nine of every 1000 babies born in the United States have a congenital heart disease. It shall be noted that there are more than 35 different known forms of CHDs such as atrial septal defect, ventricular septal defect, hypoplastic left heart syndrome and hypoplastic right heart syndrome, among others. Among all the CHDs, about 20% of them relate to a single ventricle anatomy/univentricular heart.

Generally, a normal human heart has four separate chambers, viz., right atrium, right ventricle, left atrium and left ventricle through which the blood flows. In a normal human heart, the ventricles are separated by a wall/partition (septum). Contrastingly, in a univentricular heart, the wall/septum is absent causing the deoxygenated blood from the right ventricle to mix with the oxygenated blood in the left ventricle. Therefore, the single ventricle pumps the mixture of oxygenated blood and deoxygenated blood into the lungs and to the body at high pressure. Consequently, pumping blood at high pressure into the lungs damages the fine blood vessels in the lungs and the mixture of oxygenated blood and deoxygenated blood leads to conditions such as hypoxemia, change in patient colour (cyanosis) so on and so forth.

Unfortunately, surgical procedures adopted in the univentricular heart disorder are palliative and not curative. A staged procedure known as "Fontan procedure" is the palliative procedure performed in univentricular heart disorder. The underlying principle in Fontan is, redirecting the deoxygenated blood from the inferior vena cava (IVC) and the superior vena cava (SVC) into the pulmonary artery, by-passing the right ventricle. The first stage (Norwood procedure) involves atrial septectomy and transection and ligation of the distal main pulmonary artery. The proximal pulmonary artery is then connected to the hypoplastic aortic arch, while the coarcted segment of the aorta is repaired. An aortopulmonary shunt is created to connect the aorta to the main pulmonary artery to provide pulmonary blood flow. In the second stage (Glenn procedure), the shunt to the pulmonary arteries is disconnected and the right pulmonary artery is connected directly to the SVC, the vein that brings deoxygenated blood from the upper part of the body to the heart. In the third stage (Fontan operation), the IVC is connected to the pulmonary artery via an intra-atrial or extra-cardiac connection thereby directly supplying the deoxygenated blood to the pulmonary artery.

FIG. 1 is a flowchart 100 illustrating the flow of blood in a normal human heart. At step 102 the deoxygenated blood from the body enters right atrium through the inferior vena cava (IVC) and superior vena cava (SVC). At step 104, the blood from the right atrium is pumped into the right ventricle through tricuspid valve. At step 106, the right ventricle pumps the deoxygenated blood to the pulmonary artery through pulmonary valve. At step 108, the pulmonary artery carries the deoxygenated blood to the lungs for oxygenation. At step 110, the oxygenated blood from the lungs is supplied to the pulmonary vein. At step 112, the pulmonary vein drains the oxygenated blood into the left atrium. At step 114, the left atrium pumps the oxygenated blood into the left ventricle through mitral valve. At step 116, the left ventricle pumps the oxygenated blood to the aorta through aortic valve. The aorta further supplies the oxygenated blood to various parts of the body.

FIG. 2 is a flowchart 200 illustrating the flow of blood in a fontan physiology with an extra cardiac connection. At step 202, because of the anastomosis of the SVC and pulmonary artery, the blood from the SVC directly enters the pulmonary artery. At step 204, the blood from the IVC enters the artificial heart implant (typically a graft) that is anastomosed with it. At step 206, the blood from the artificial heart implant enters the pulmonary artery. At step 208, the pulmonary artery carries the deoxygenated blood to the lungs for oxygenation. At step 210, the oxygenated blood from the lungs is supplied to the pulmonary vein. At step 212, the pulmonary vein drains the oxygenated blood into the left atrium. At step 214, the left atrium pumps the oxygenated blood into the left ventricle through mitral valve. At step 216, the left ventricle pumps the oxygenated blood to the aorta through aortic valve from where the oxygenated blood is supplied to various parts of the body.

Therefore, the problem of mixture of deoxygenated blood and oxygenated blood in the single ventricle is negated. However, in 20-30% of the cases, wherein the patient has undergone Fontan procedure, heart transplant is required eventually. Some of the long term consequences of the Fontan procedure includes thromboembolism caused due to the turbulent flow of blood at the junction of IVC, SVC and pulmonary artery, poor exercise tolerance with advancing age, chronic venous hypertension and the like.

Over the years, surgeons and scientists have proposed different intra-atrial and extra-cardiac connections to minimize the consequences of the Fontan procedure. Desai et al. in their publication titled *Haemodynamic comparison of a novel flow-divider Optiflo geometry and a traditional total cavopulmonary connection* published in *Interactive Cardio-Vascular and Thoracic Surgery*, volume 17 (2013) proposed an extra-cardiac IVC graft to bifurcate the flow of blood from the IVC. The graft is typically a cylindrical conduit that connects the IVC and the pulmonary artery. Further, a triangular prismatic insert is placed at the distal end of the IVC graft such that one lateral edge of the prism faces the blood flowing from the IVC. Such a configuration bifurcates the blood that comes in contact with the insert thereby directing the blood towards the right and left pulmonary artery. However, the above device has two major disadvantages. Firstly, the IVC graft fails to bifurcate the SVC flow, wherein the blood flowing from the SVC is directly incident on the flat lateral face of the insert thereby causing a disturbance in flow (turbulence). This disturbance in flow results in the same consequences as in the conventional fontan procedure such as loss in energy, thromboembolism and the like. Secondly, the placing of the insert inside a graft further constricts the path of flow of blood near the distal end of the graft. The constriction in the flow path results in an increase in convective flow acceleration and drop in pressure of the blood entering the pulmonary artery. Therefore, the flow entering the lungs does not have enough pressure to overcome the pulmonary vascular resistance offered by the lungs thereby resulting in poor oxygenation of the blood.

Similarly, the U.S. Pat. No. 7,811,244 discloses an extra-cardiac implant for total cavopulmonary connection (TCPC), wherein the implant has a cross shaped external framework that houses a centre piece for bifurcating the blood flow. In one embodiment (Optiflo 200), the centre piece has a diamond like configuration to address the issue of small SVCs that are not suitable for division or anastomosis. However, the centre piece configuration does not extend into the lumen of the SVC thereby failing to address the bifurcation of the SVC flow. The implant as disclosed in U.S. Pat. No. 7,811,244 has associated disadvantages. Firstly, the SVC flow is not bifurcated thereby causing a turbulence at the junction of the SVC flow and IVC flow. As explained earlier, turbulence in the blood flow results in undesirable consequences. Secondly, the external framework in Optiflo 200 is cross-shaped, wherein the framework comprises four cylinders that are configured to be anastomosed to the IVC, SVC, right pulmonary artery and left pulmonary artery respectively. Further, a centre piece is placed within this cross-shaped framework whose inferior end located in that part of the framework where the IVC blood flows towards the confluence. The diameter of this part of the device is uniform. Such a configuration of the graft constricts the space available for the fluid during its transit from IVC to the confluence as mentioned afore thereby causing an increase in convective flow acceleration and a drop in the pressure of the blood entering the lungs. Finally, the implant requires a quadruple anastomosis, wherein a portion of IVC, SVC and pulmonary artery are removed, and the implant is anastomosed to the ends of the native IVC, SVC and pulmonary artery. This procedure results in surgical complexity and a significant loss of native tissue which is undesirable.

In view of the foregoing, it is evident that there is a need for an improved artificial heart implant for addressing the foresaid problems.

SUMMARY

In an embodiment, the device for use in total cavopulmonary connection comprises a hollow body and a flow separator. The hollow body further comprises a first end that is configured to receive blood from inferior vena cava and a second end configured to be connected to pulmonary artery. Further, the flow separator aids in guiding blood from inferior vena cava and superior vena cava to right pulmonary artery and left pulmonary artery. The flow separator comprises an inferior end and a superior end. The inferior end is located between the first end and the second end of the hollow body and further the flow separator is dimensioned to have the superior end enter superior vena cava when the second end is connected to the pulmonary artery.

BRIEF DESCRIPTION OF DRAWINGS

Embodiments are illustrated by way of example and not limitation in the figures of the accompanying drawings, in which like references indicate similar elements and in which.

DETAILED DESCRIPTION

The following detailed description includes references to the accompanying drawings, which form a part of the detailed description. The drawings show illustrations in accordance with example embodiments. These example embodiments, which may be herein also referred to as "examples" are described in enough detail to enable those skilled in the art to practice the present subject matter. However, it may be apparent to one with ordinary skill in the art, that the present invention may be practised without these specific details. In other instances, well-known methods, procedures and components have not been described in detail so as not to unnecessarily obscure aspects of the embodiments. The embodiments can be combined, other embodiments can be utilized, or structural, logical, and design changes can be made without departing from the scope of the claims. The following detailed description is, therefore, not to be taken in a limiting sense, and the scope is defined by the appended claims and their equivalents.

In this document, the terms "a" or "an" are used, as is common in patent documents, to include one or more than one. In this document, the term "or" is used to refer to a nonexclusive "or," such that "A or B" includes "A but not B," "B but not A," and "A and B," unless otherwise indicated.

Figure 1:
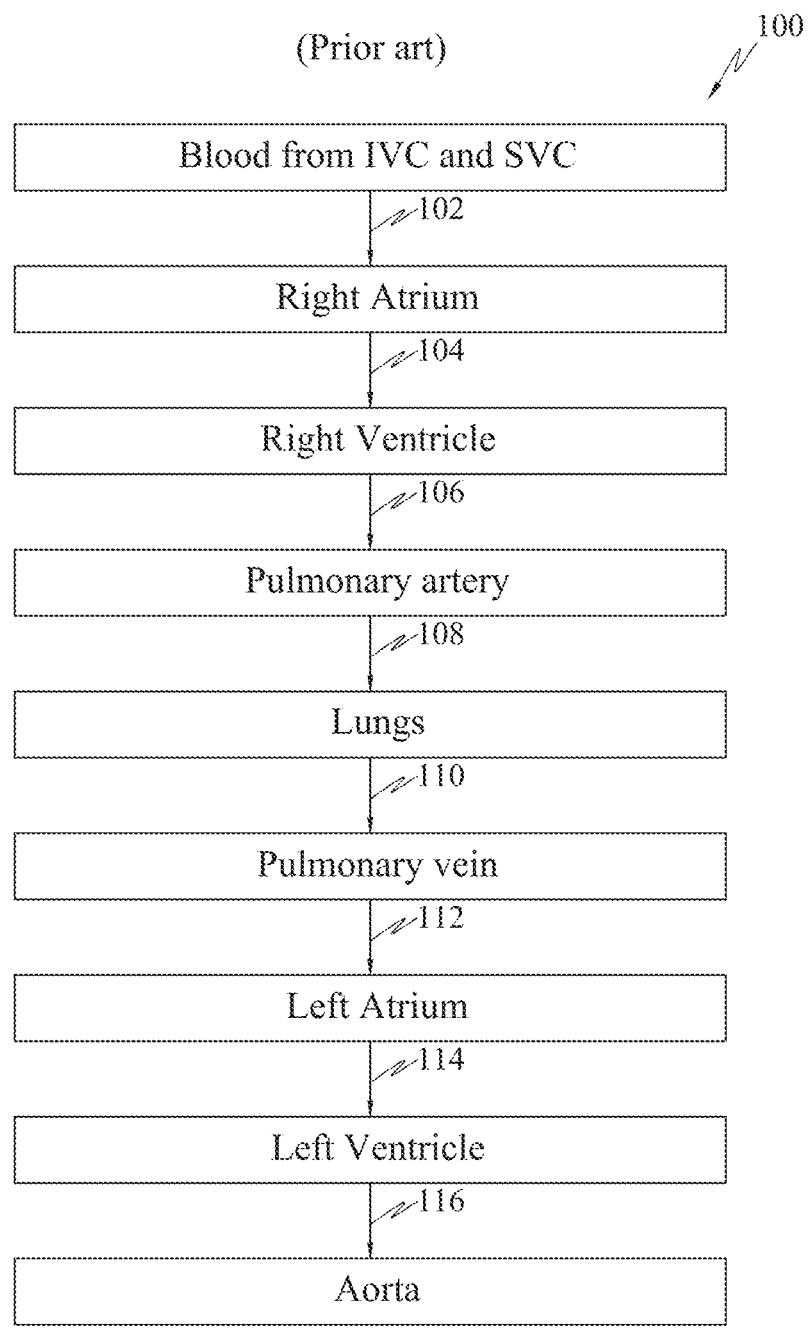
FIG. 1 is a flowchart 100 illustrating the flow of blood in a normal human heart.
Figure 2:
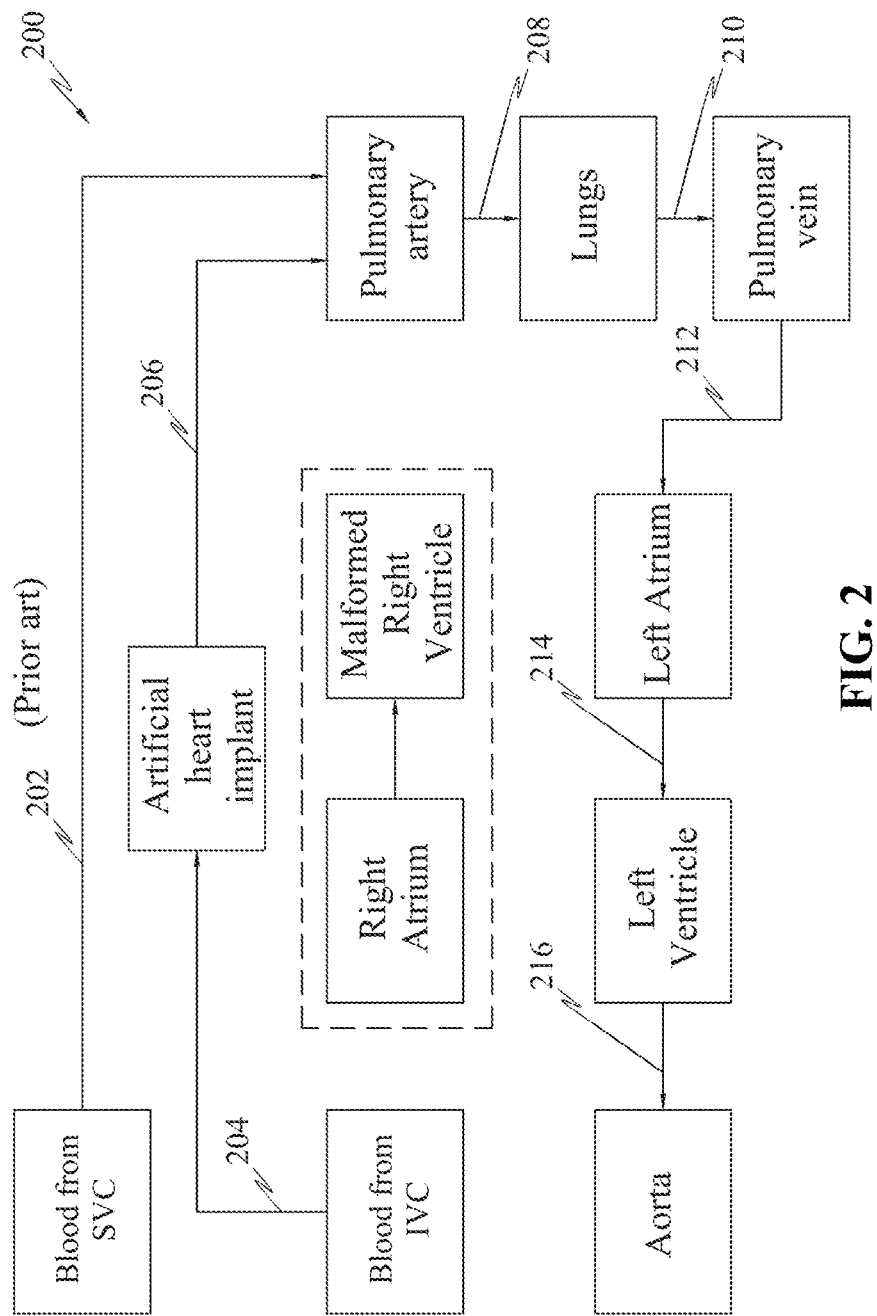
FIG. 2 is a flowchart 200 illustrating the flow of blood in a fontan physiology with an extra cardiac connection.
Figure 3:
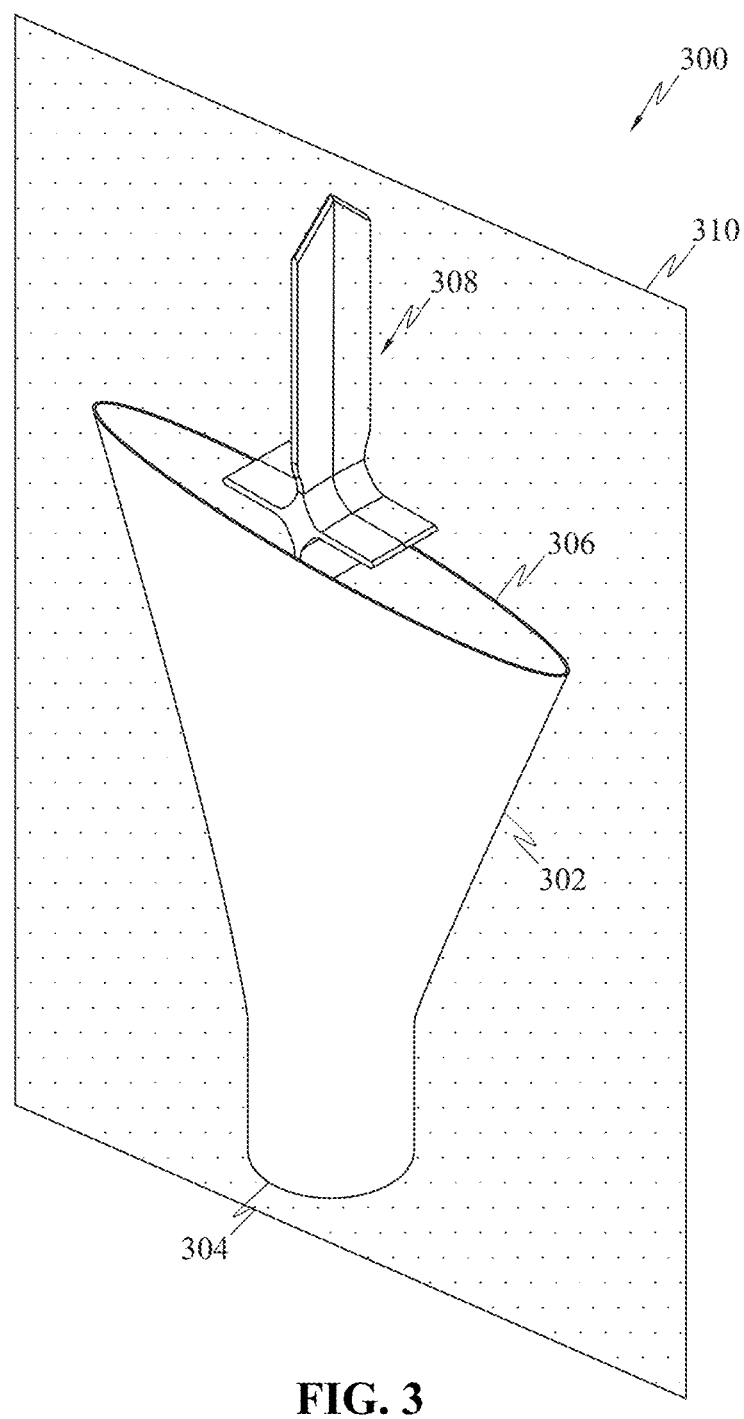
FIG. 3 illustrates a device 300 for use in total cavopulmonary connection, in accordance with an embodiment.

Referring to the figures, FIG. 3 illustrates a device 300 for use in total cavopulmonary connection, in accordance with an embodiment. The device 300 comprises a hollow body 302 and a flow separator 308. The hollow body 302 may be configured to serve as a passage of blood flow and the flow separator 308 may be configured to bifurcate the blood that is flowing from the IVC and SVC.

In an embodiment, the hollow body 302 may be funnel shaped.

In an embodiment, the hollow body 302 may enclose at least a portion of the flow separator 308 in a manner that the flow separator 308 divides the hollow body 302 into volumetric chambers.

In an embodiment, the device 300 may be made of materials including but not limited to teflon, dacron, or stretched polytetrafluoroethylene (PTFE) (such as GORE-TEX).

In an embodiment, the hollow body 302 may comprise a first end 304 and a second end 306. The first end 304 may be configured to be anastomosed to the IVC in an end to end manner and the second end 306 may be configured to be anastomosed to the pulmonary artery in an end to side manner.

In an embodiment, the first end 304 may have a circular cross-section and the second end 306 may have an elliptical cross-section. Further, the diameter of the first end 304 may be in the range of 18 mm to 22 mm and the length of the major axis of the ellipse is in the range of 38 mm to 42 mm. In an embodiment, ratio between the dimension of the major axis and the dimension of the first end along the lateral axis is in the range of 1.72 to 2.33. Therefore, the hollow body 302 may define a configuration that diverges from the first end 304 to the second end 306 to define a smooth curvature. The divergent configuration of the hollow body 302 offers more space near the confluence of the device 300 and pulmonary artery for the flow of blood thereby minimizing the pressure drop in the blood flow entering the pulmonary artery.

In an embodiment, the second end 306 is anastomosed to the pulmonary artery in an end to side manner, wherein the suture line horizontally spans from the distal end of right pulmonary artery (pre-branching) to the main pulmonary artery.

In an embodiment, the distance between the first end 304 and the second end 306 may be equal to the distance between IVC end at the diaphragmatic level and the inferior border of the right pulmonary artery, opposite to bi-directional Glenn anastomotic site.

In an embodiment, the distance between the first end 304 and the second end 306 varies from patient to patient but is typically in the range of 70 mm to 90 mm.

Figure 6:
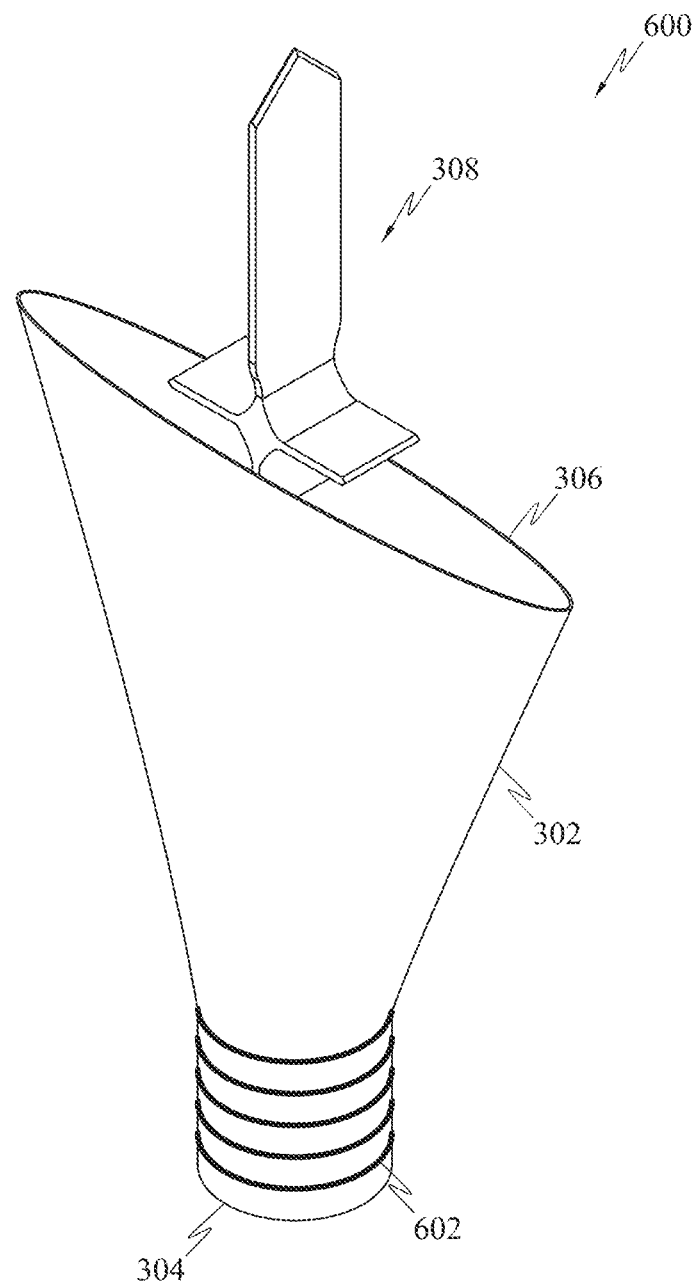
FIG. 6 illustrates a device 600 for use in total cavopulmonary connection, in accordance with another embodiment.

Referring to FIG. 6, in another embodiment of the device 600, the first end 304 of the hollow body 302 may be comprise a wire reinforcement 602. The wire reinforced first end 304 typically extends for about 30 mm to 40 mm and may be configured to be inserted into the lumen of the IVC. Such a configuration negates the requirement to incise/ligate/divide the IVC and suture the end of the IVC to the first end 304. Therefore, only one suture line (between second end 306 and pulmonary artery) is required to affix the device 300 to the heart. Further, such configuration minimizes the excessive loss of native tissue as in existing technologies.

In another embodiment, a surface of the hollow body 302 may comprise a fenestration of 5 mm/6 mm diameter measuring 20 mm to 30 mm in length is configured to be sutured to the wall of the right atrium. In such a configuration, the part of the blood from the IVC that is received at the first end 304 is directed into the right atrium through the fenestration. Therefore, when the pressure in the veins is high, some of the oxygen-poor blood can escape through the fenestration to relieve the pressure.

Figure 4A:
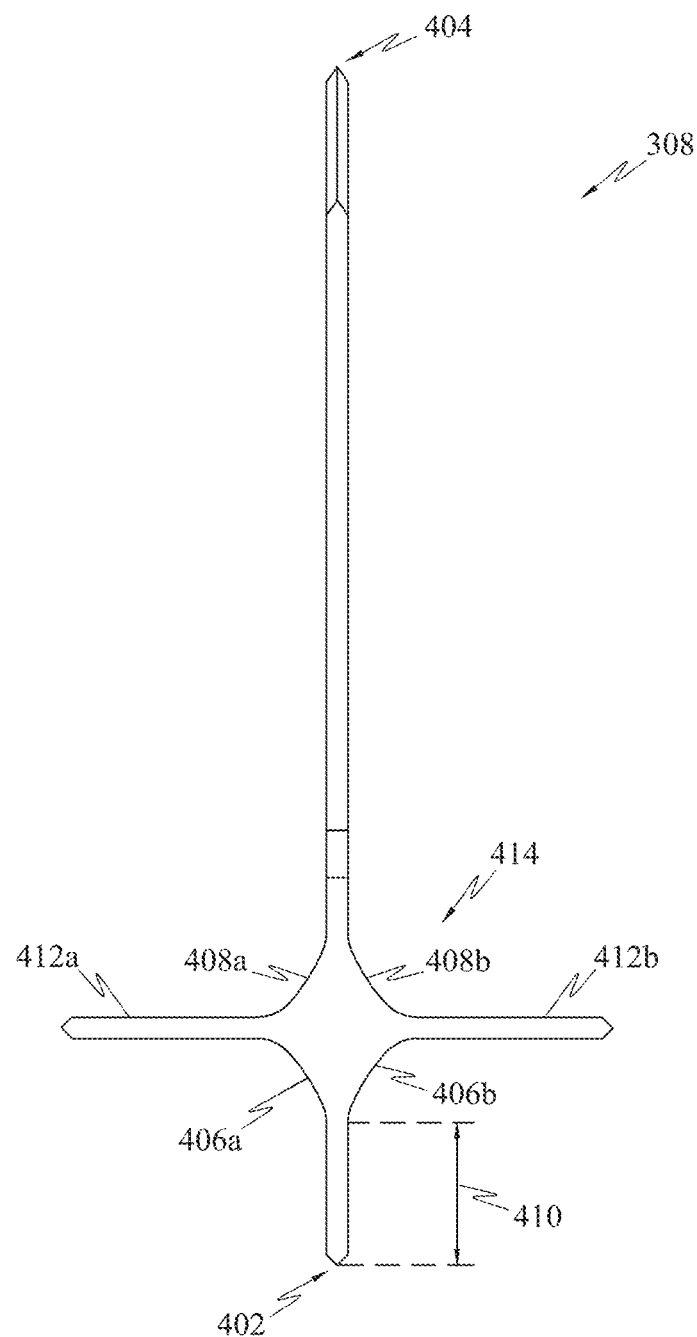
FIG. 4A illustrates a flow separator 308 of the device 300, in accordance with an embodiment.

FIG. 4A illustrates the flow separator 308, in accordance with an embodiment. The flow separator 308 may comprise an inferior end 402, a centre piece 414 and a superior end 404. The inferior end 402 of the flow separator 308 may be disposed between the first end 304 and the second end 306 of the hollow body 302 and the superior end 404 may be configured to extend into the lumen of the SVC.

In an embodiment, the flow separator 308 may comprise uniformly spaced markings on its exterior surface thereby enabling the surgeon to accurately position the device 300 during the surgical process.

In an embodiment, the centre piece 414 may comprise a first pair of concave channels (406a and 406b) that converges towards the IVC to define an inferior portion 410 that resembles a plate. The inferior portion 410 terminates inside the hollow body to define the inferior end 402. The blood from the IVC interfaces with the inferior end 402 and gets bifurcated. Further, the blood from the IVC flows along the sides of the inferior portion 410 and reaches the first pair of concave channels (406a and 406b), wherein the first pair of concave channels (406a and 406b) guides the flow into the right and left pulmonary artery.

In an embodiment, the inferior portion 410 extends to a distance of 6 mm into the hollow body 302.

In another embodiment, the flow separator 308 is cantilevered onto the hollow body 302 about the inferior portion 410.

In an embodiment, the inferior end 402 may be configured to bifurcate IVC flow, the centre piece 414 may be configured to bifurcate bi-caval flow and the superior end 404 may be configured to bifurcate SVC flow.

In an embodiment, the centre piece 414 may define a star configuration and is disposed exterior to the hollow body 302.

Figure 4B:
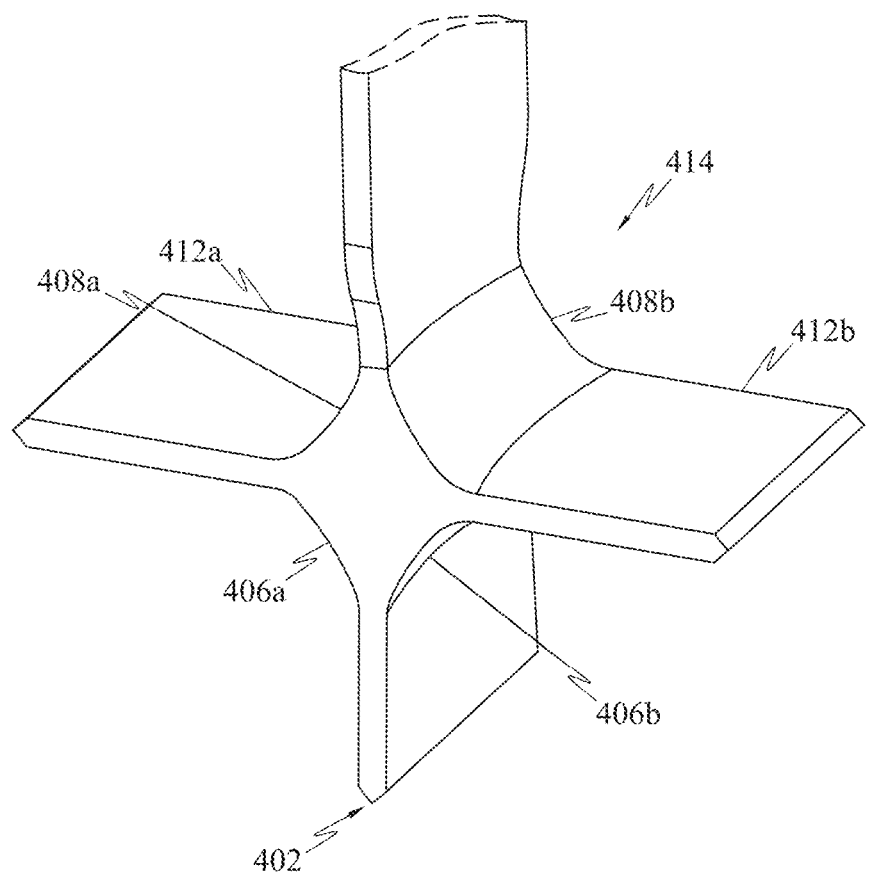
FIG. 4B illustrates a detailed view of flow separator 308 of the device 300, in accordance with an embodiment.

Referring to FIG. 4B, a second pair of concave channels (408a and 408b) may adjoin the first pair of concave channels (406a and 406b) and extends into lateral projections (412a and 412b). Further, the second pair of concave channels (408a and 408b) is configured to face the blood from the SVC. The centre piece 414 may be defined such that the distance between the longitudinal edges is 8 mm and the distance between lateral edges is 8 mm. The lateral projections may have a length of 10 mm.

In an embodiment, the superior end 404 of the flow separator 308 may be tapered such that it enables easy insertion of the superior end 404 into the lumen of the SVC. Further, the tapered superior end 404 may define a wedge. The wedge is configured such that the blood from the SVC interfaces with the superior end 404 and gets bifurcated. Further, the bifurcated blood flow reaches the second pair of concave channels (408a and 408b) that is configured to direct the blood towards the right and left pulmonary artery. Finally, the lateral projections (412a and 412b) smoothly direct the blood into the pulmonary arteries. Therefore, the flow separator 308 aids in bifurcating the SVC flow as well as the IVC flow.

In an embodiment, the centre piece 414 is positioned inside the pulmonary artery in a manner that about one-third total volume of blood flowing through the pulmonary artery is the blood from SVC and about two-third total volume of blood flowing through the pulmonary artery is the blood from IVC.

In an embodiment, the device 300 is affixed to a human heart in a manner that the inferior portion 410 may lie within the hollow body 302 bifurcating the IVC flow. Further, the centre piece 414 may lie within the pulmonary artery and the superior end 404 may traverse into the lumen of the SVC bifurcating the SVC flow.

Figure 5A:
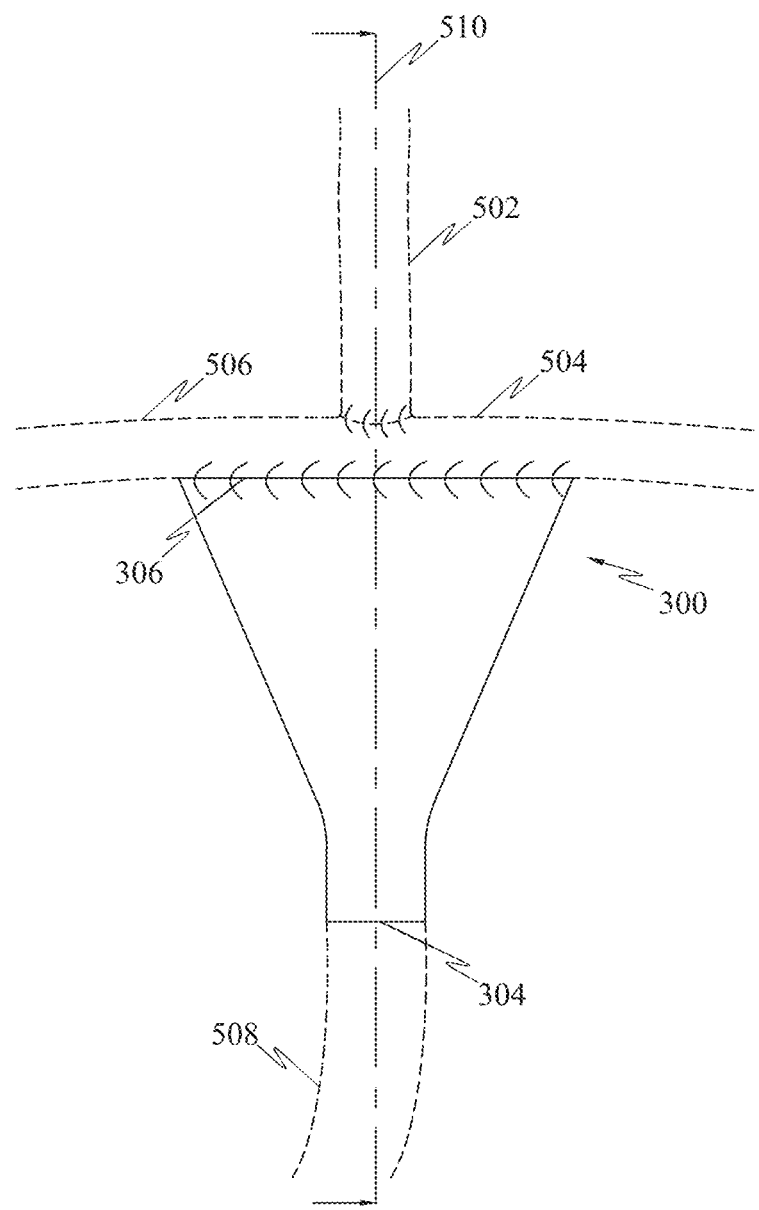
FIG. 5A illustrates the device 300 affixed to a human heart, in accordance with an embodiment.

FIG. 5A illustrates the device 300 affixed to a human heart, in accordance with an embodiment. The first end 304 of the hollow body 302 may be anastomosed to the IVC 508 and the second end 306 of the hollow body 302 may be anastomosed to the pulmonary artery in an end to side manner. Further, the SVC 502 is anastomosed to the pulmonary artery. Therefore, the blood from the SVC 502 and IVC 508 are directed into the right 506 and left 504 pulmonary artery by-passing the right atrium.

Figure 5B:
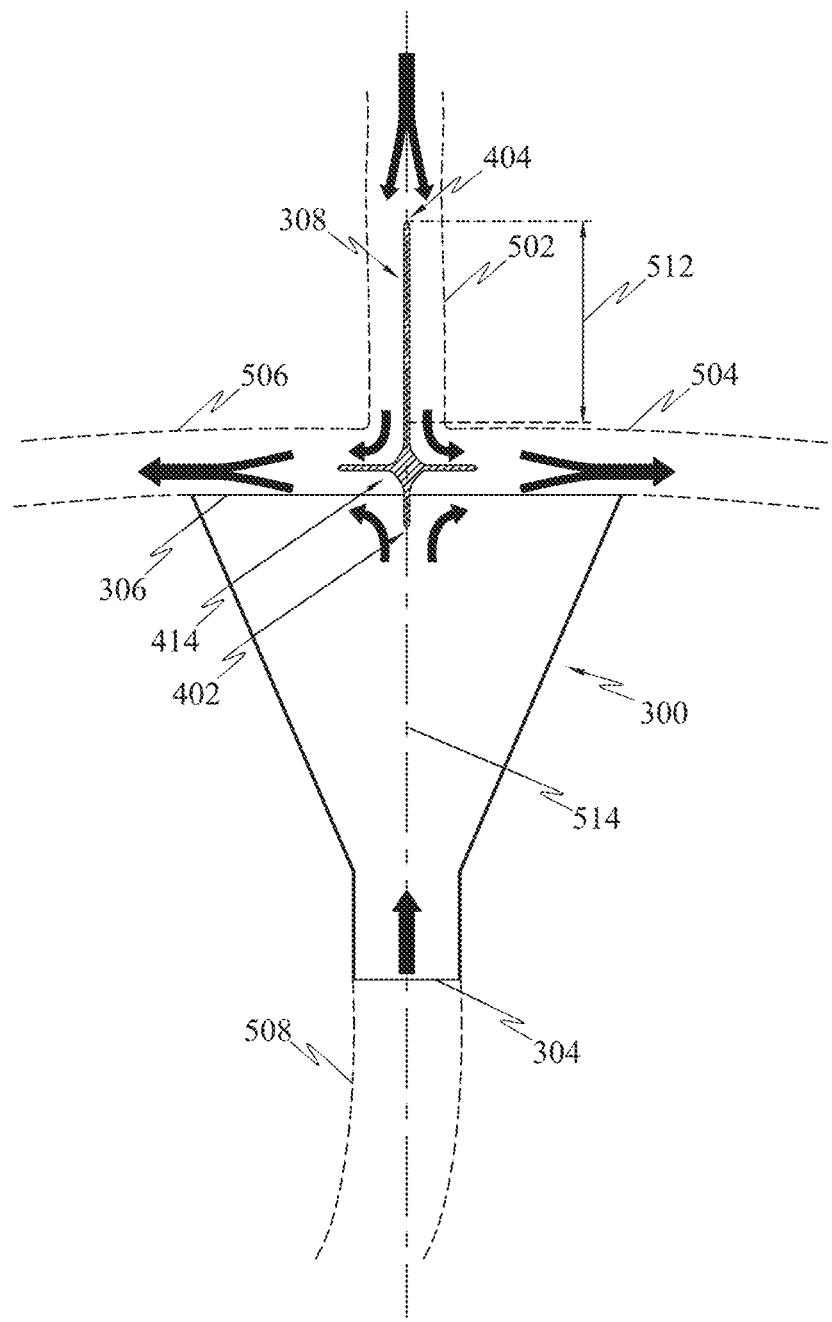
FIG. 5B illustrates the sectional view of the device 300 affixed to a human heart along the plane 310.

FIG. 5B illustrates the sectional view of the device 300 affixed to a human heart along the plane 310. As can be seen, the flow separator 308 comprises a superior portion 512 that extends into the lumen of the SVC 502. The superior end 404 bifurcates the flow from the SVC 502 and directs it into right pulmonary artery 506 and left pulmonary artery 504. The inferior end 402 bifurcates the flow from the IVC 508 and directs it into right 506 and left 504 pulmonary arteries. Hence, the flow of blood from IVC 508 and SVC 502 are directed into the pulmonary artery with minimal or no flow disturbance (turbulence).

In an embodiment, the superior portion 512 of the flow separator 308 may traverse into the SVC 502 lumen for about 20 mm to 30 mm dividing the SVC 502 into equal halves.

In an embodiment, the inferior portion 410 of the flow separator 308 may be positioned along the longitudinal axis 514 of the hollow body 302 thereby equally distributing the blood from the IVC into the right 506 and left 504 pulmonary arteries. It is a well-established fact that when equal amount of blood goes to right 506 and left 504 pulmonary arteries, the possibilities of pulmonary arterio-venous malformation arising are almost minimal.

Figure 5C:
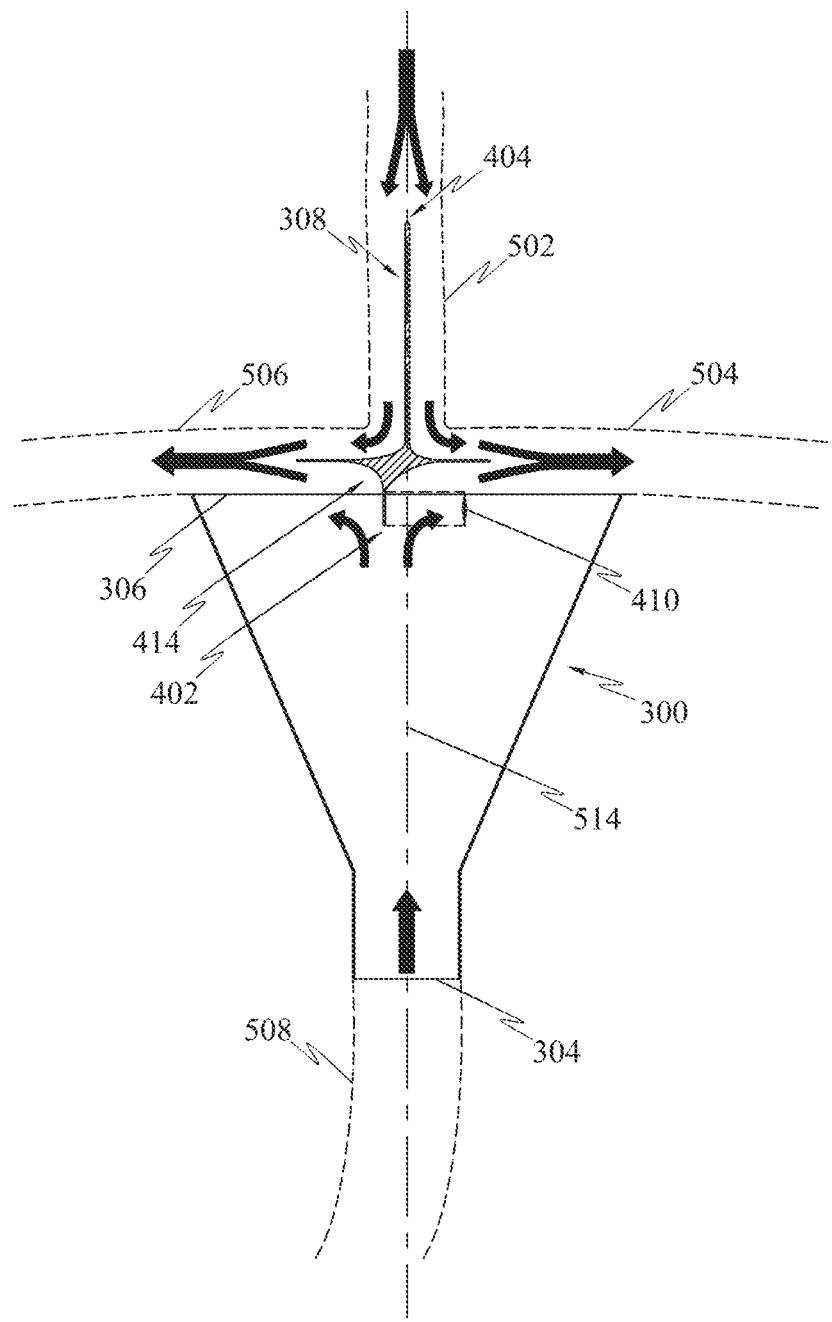
FIG. 5C illustrates the sectional view of an alternate embodiment of the device 300 affixed to a human heart along the plane 310.

Referring to FIG. 5C, the inferior portion 410 of the flow separator 308 may be offset from the longitudinal axis 514 of the hollow body 302. By offsetting the inferior portion 410 of the flow separator 308, the IVC flow into one lung is increased and IVC flow into another lung is decreased. This configuration aids in increasing the quantum of blood flow to the lung that has higher pulmonary resistance.

Figure 5D:
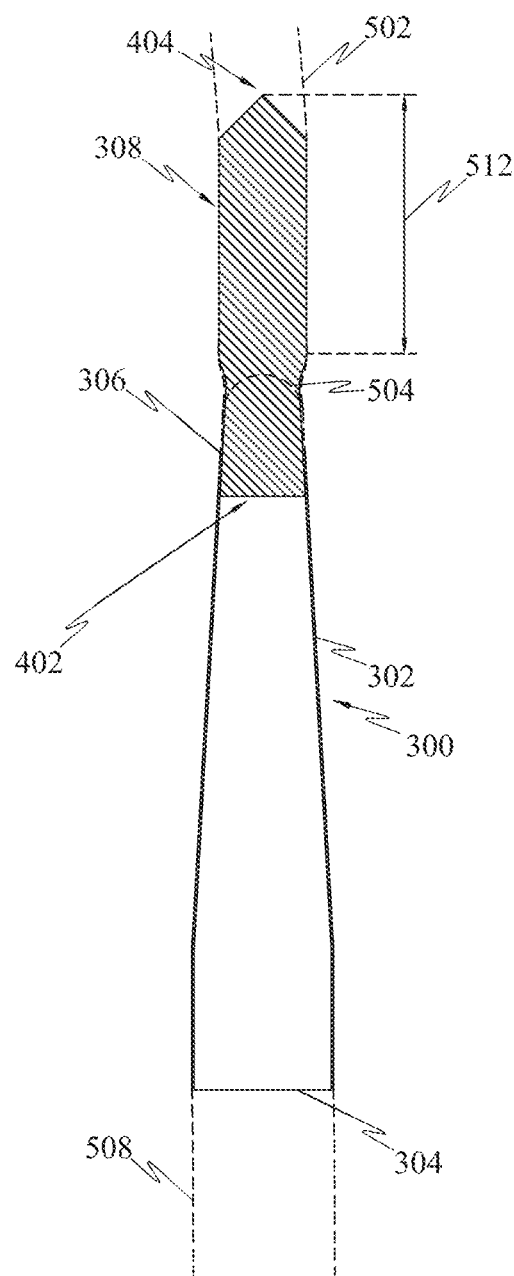
FIG. 5D illustrates the sectional view of the device 300 affixed to a human heart along the plane 510.

FIG. 5D illustrates the sectional view of the device 300 affixed to a human heart along the plane 510. As can be seen, the inferior portion 410 of the flow separator 308 may be attached to the anterior and posterior sides of the hollow body 302. Further, the height of the flow separator 308 may vary along its length. As an example, the height of the inferior portion of the flow separator 308 that is within the hollow body may be 18 mm, the height of the centre piece of the flow separator 308 that is within the lumen of the pulmonary artery may be 12 mm and the height of the superior portion of the flow separator 308 that is within the lumen of the SVC 502 may be 14 mm.

Figure 7:
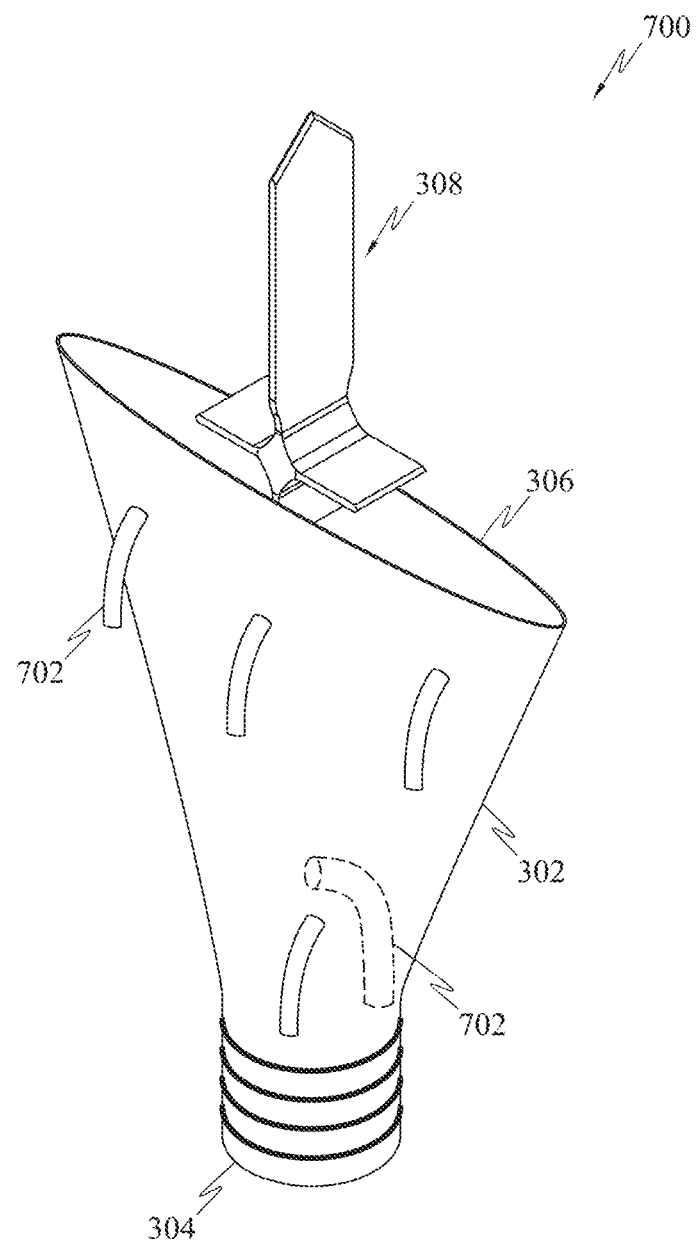
FIG. 7 illustrates a device 700 for use in total cavopulmonary connection, in accordance with yet another embodiment.

FIG. 7 illustrates an alternate embodiment of the device 700 discussed previously. The device 700 comprises the hollow body, wherein a surface of the hollow body 302 may comprise a plurality of ports 702. The ports 702 provide access to the probes to enter the pulmonary artery, SVC and IVC. Typically, the probes are measurement devices capable of measuring parameters like pressure, velocity, flowrate and every conceivable hemodynamic data. In general, 1 mm ports of length 3 mm to 4 mm are disposed on the surface of the hollow body 302.

Figure 8:
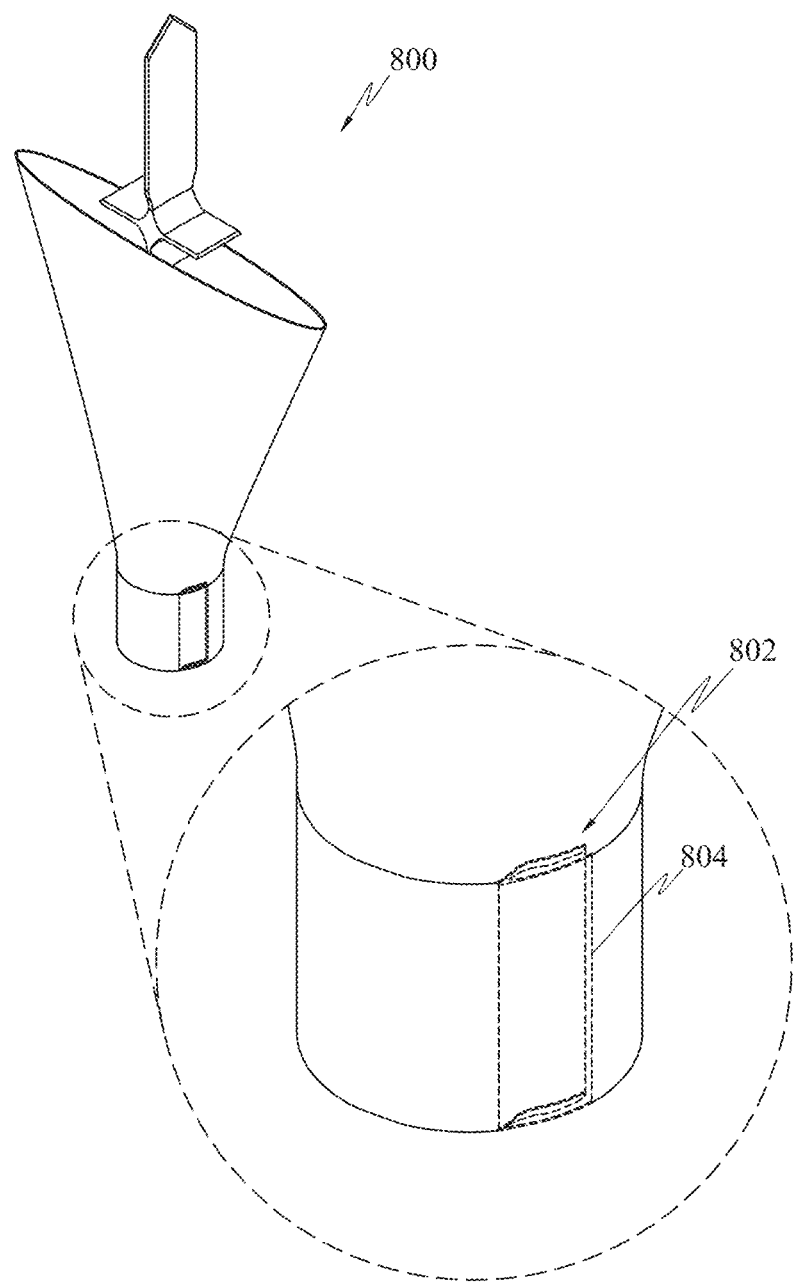
FIG. 8 illustrates a device 800 for use in total cavopulmonary connection, in accordance with yet another embodiment.

Referring to FIG. 8, in another embodiment of the device 800, the first end 304 of the hollow body 302 may have a crimped configuration 802, wherein the first end 304 may be folded to form a crimp 802 of width in the range of 1 mm to 2 mm and further a tear seam 804 may be formed at the folded crimp 802. Further, the diameter of the first end 304 may be increased by 1 mm to 2 mm by breaking the tear seam 804 of the crimp. Generally, the Fontan procedure is performed on a patient of 18-24 months of age. As the patient grows, diameter of IVC increases accordingly which results in a mismatch between the IVC and the first end 304 of the hollow body 302. This can be overcome by the use of foresaid crimped configuration of the hollow body 302, wherein years after the Fontan procedure, a catheter can be inserted into the hollow body 302 to inflate inside the first end 304 thereby breaking the tear seam 804 and expanding the diameter of the first end 304 of the hollow body 302.

Figure 9:
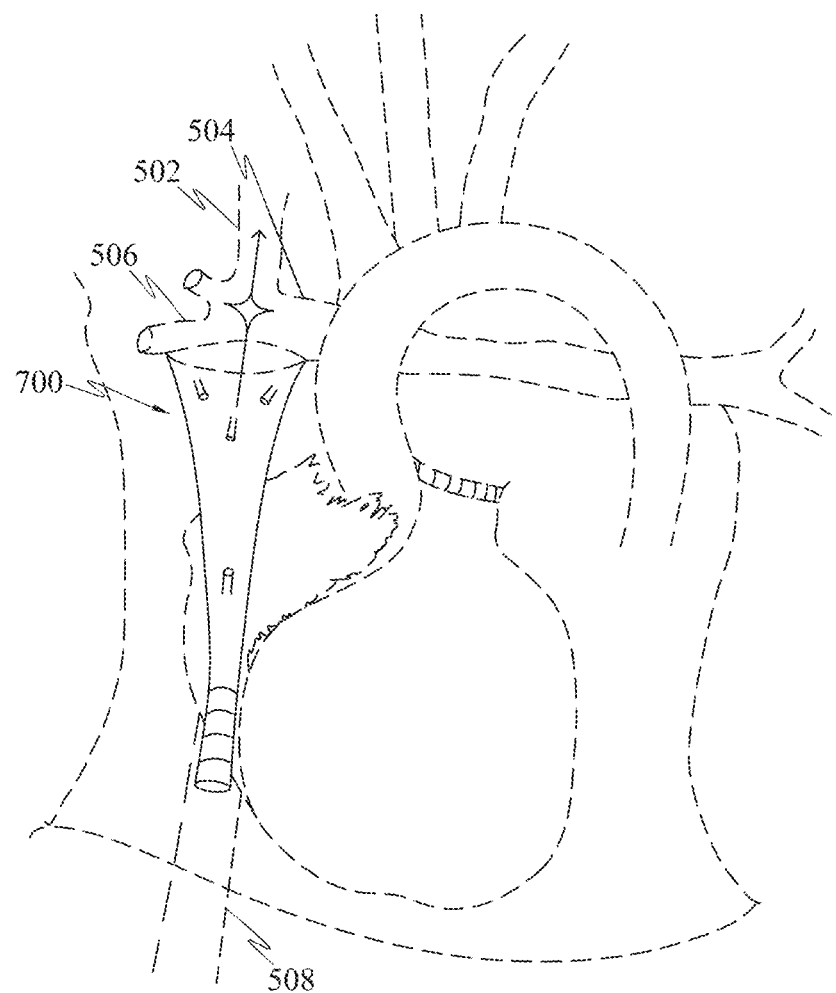
FIG. 9 represents an artistic impression of the device 700 affixed to a human heart.

FIG. 9 represents an artistic impression of the device 700 affixed to a human heart. The device 700 has its wire reinforced first end 304 connected to the IVC 508 in an end to end manner and second end 306 anastomosed to pulmonary artery in an end to side manner.

Simulation Results

Multiple simulation studies were performed on the device 300 along with a conventional offset extracardiac total cavopulmonary connection (OCPC) and Y graft total cavopulmonary connection (YCPC). Each of the extracardiac connections has corresponding three different configurations, viz., simple geometric model (SGM), paediatric model and adult model on which flow simulations were performed. Poor exercise tolerance with advancing age is a known issue with Fontan patients. In order to determine the performance of the extracardiac connections under exercise conditions, exercise conditions are numerically imposed upon each configuration by doubling and tripling the baseline IVC flow rate. However, the SVC flow rates are maintained constant as in other similar studies. Therefore, the simulation studies are performed under three different conditions, viz., resting (1×), moderate (2×) and exercise (3×) conditions.

Hemodynamics

The flow of blood through the TCPC is studied under different conditions. It is observed that at resting flow state, in OCPC, there is a preferential flow towards the left pulmonary artery (LPA). Further, there is a collision of SVC and IVC flows resulting in turbulence and vortices at the confluence. Therefore, OCPC resulted in unfavourable results.

In YCPC, particularly SGM and paediatric model, an orderly flow of IVC blood via the two limbs of the Y graft is observed. However, the SVC flow is incident directly on the wall of the pulmonary artery (PA) resulting in a turbulence. This turbulent flow further enters the LPA and RPA and affects the IVC flow as well. In adult model, turbulence is observed in the proximal end of LPA. Also, the SVC flow telescopes through the IVC flow causing vortices and zones of recirculation within the LPA, which also propagates downstream.

In the device 300, the superior end 404 of the flow separator 308 bifurcates the SVC flow equally into the LPA and RPA. The IVC flow also is uniformly bifurcated by the inferior portion 410 of the flow separator 308. The bifurcated flows are further smoothly directed into the RPA and LPA by the centre piece 414. It can also be observed that the streamlined IVC and SVC flows occupy separate segments within the lumen of the PA thereby minimizing the power loss caused by the collision of the flows.

Power Loss

Figure 10:
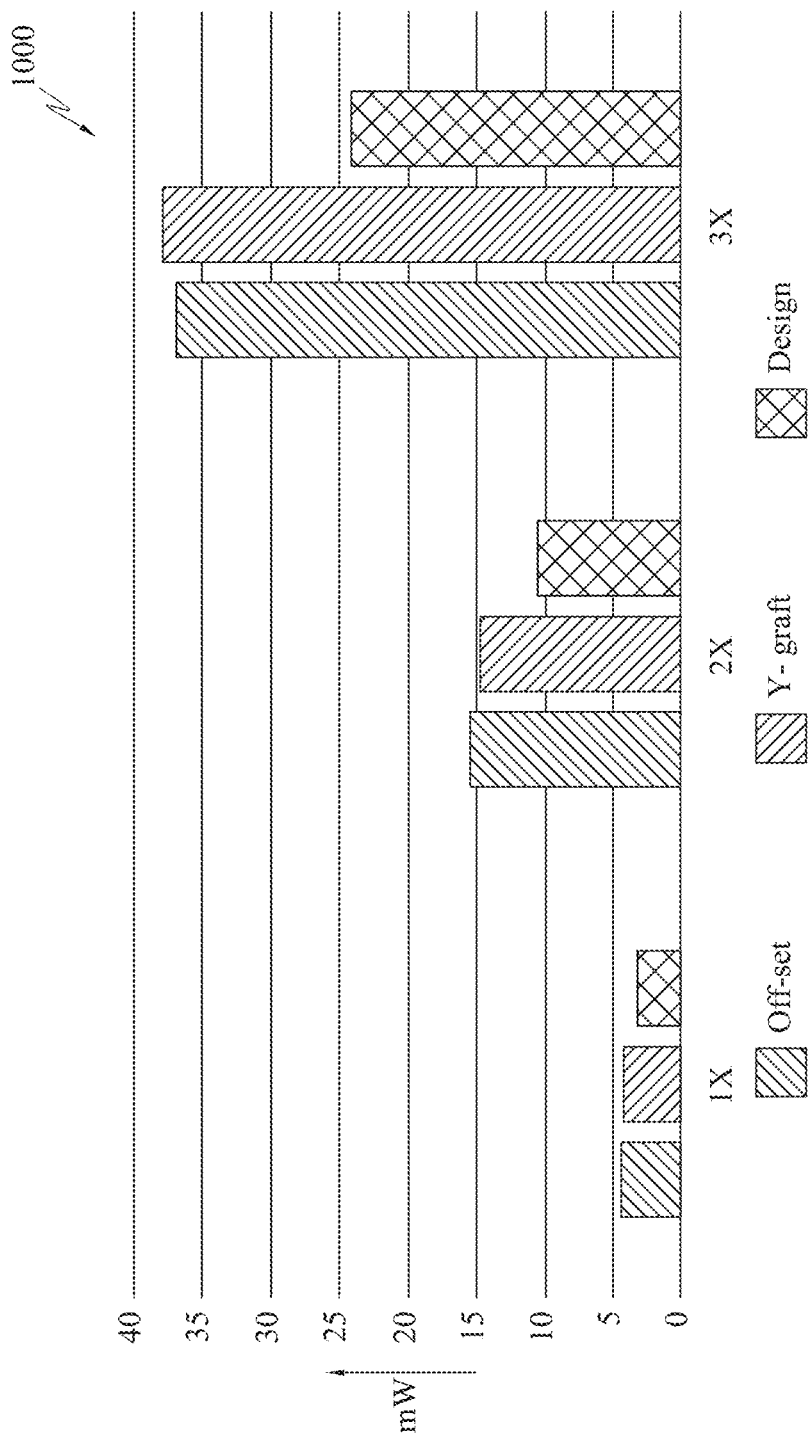
FIG. 10 is a bar chart 1000 that illustrates a graphical representation of power loss in the device 300 in comparison to the prior art.

FIG. 10 is a bar chart 1000 that illustrates a graphical representation of power loss in the device 300 in comparison to the prior art. The power loss in adult configuration for three models viz., OCPC (Offset), YCPC (Y-graft) and the device 300 (Design) under three different conditions is illustrated. It is understood that the device 300 performs better than the prior art under all three conditions.

Table 3 represents the power loss in the models under different flow conditions.

TABLE 3

| | | Power loss (mW) | | |
|---|---|---|---|---|
| Configuration | Model | 1X | 2X | 3X |
| SGM | OCPC | 1.65 | 6.25 | 13.69 |
| | YCPC | 1.35 | 5.21 | 11.53 |
| | Device 300 | 1.29 | 4.95 | 11.00 |
| Paediatric | OCPC | 1.96 | 8.05 | 17.91 |
| | YCPC | 1.76 | 6.76 | 14.65 |
| | Device 300 | 1.69 | 6.42 | 13.88 |
| Adult | OCPC | 4.46 | 15.44 | 36.84 |
| | YCPC | 4.25 | 14.69 | 37.95 |
| | Device 300 | 3.31 | 10.49 | 24.18 |

As can be seen, under resting condition (1×), all the three models exhibit nearly same power loss. However, under exercise conditions (2× and 3×), the OCPC shows significant power loss as compared to YCPC and the device. The device exhibits the least power loss among other models considered.

In the adult configuration, the YCPC exhibits highest power loss under exercise conditions closely followed by the OCPC. The device 300 exhibits power loss that is significantly lesser than that of the OCPC and YCPC models. Therefore, it is clear that the device 300 performs well under exercise conditions.

IVC Flow Distribution

The following Table. 4 lists the percentage of IVC blood that enters the right pulmonary artery (RPA).

TABLE 4

| | | IVC flow split (RPA %) | | |
|---|---|---|---|---|
| Configuration | Model | 1X | 2X | 3X |
| SGM | OCPC | 36.8% | 47.4% | 47.4% |
| | YCPC | 52.4% | 52.4% | 52.4% |
| | Device 300 | 50.0% | 50.0% | 50.0% |
| Paediatric | OCPC | 21.1% | 26.3% | 36.8% |
| | YCPC | 52.6% | 52.6% | 52.6% |
| | Device 300 | 55.0% | 55.0% | 55.0% |
| Adult | OCPC | 13.3% | 35.7% | 33.3% |
| | YCPC | 57.5% | 50.0% | 50.0% |
| | Device 300 | 50.0% | 55.0% | 55.0% |

It is clear that the OCPC has an offset configuration that results in $2/3^{rd}$ of the total flow towards the LPA. This uneven flow distribution affects the oxygenation of the blood in the lungs. It can be seen that YCPC exhibits a perfect 50/50 split, especially in exercise conditions. The device 300 exhibits a reasonable split ratio of 55-45% across all the flow conditions.

Hepatic Blood Flow Distribution

It is reported that in as many as 25% of the patients who have undergone cavopulmonary anastomosis, pulmonary arteriovenous malformation occurs after few years. It is well known that the hepatic blood (blood from the liver) that admixes with the IVC blood contains factors that are inhibitors of vascular proliferation and remodelling. Therefore, each lung has to receive an adequate amount of hepatic blood to prevent the PAVM formation. As the minimum amount of hepatic blood required to prevent PAVM is unknown, it is preferable to achieve an equal distribution of hepatic blood to both lungs.

In a balanced pulmonary vascular resistance (PVR), the OCPC tends to supply an increased hepatic flow towards the LPA because of the offset position of the extracardiac connection. However, both the device and YCPC enables an equal splitting of hepatic blood to the RPA and LPA because of their symmetric geometries.

In an unbalanced PVR (increased left lung PVR), the offset configuration of the OCPC enables in an equal split of hepatic flow to RPA and LPA. The offset configuration results in increased flow towards the LPA and because left lung has higher PVR, the increased blood flow into the left lung compensates for the equal distribution of hepatic blood.

In YCPC, there is an unequal split of hepatic flow in unbalanced PVR. As the resistance offered by the left lung is higher, the flow naturally tends to take direction towards the path that offers least resistance. Therefore, the left lung receives less hepatic flow which might result in PAVM.

In the device 300, the equal distribution of hepatic blood flow in an unbalanced PVR is achieved by offsetting the inferior portion of the flow separator along the longitudinal axis of the hollow body. By shifting the inferior portion 410 of the flow separator 308 towards the right side, the quantum of hepatic blood flow to the left lung can be increased thereby minimizing the chances of PAVM formation.

Figure 11:
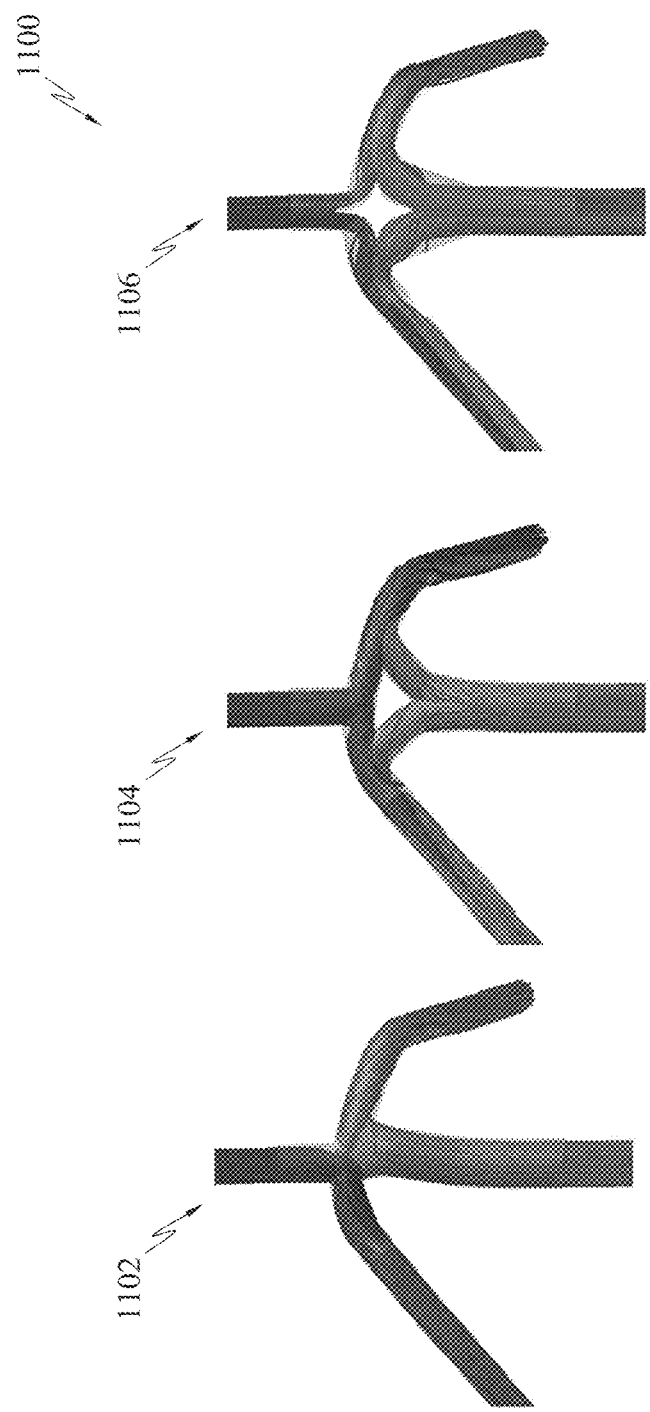
FIG. 11 illustrates simulation results 1100 showing streamlines of the flow in the device 300 and prior art.

FIG. 11 illustrates simulation results 1100 showing streamlines of the flow in the device 300 and prior art. In the figure, 1102 represents conventional offset Fontan procedure, 1104 represents conventional Y-graft procedure and 1106 represents the device 300.

Advantages Realized Over Prior Art

The device 300 as disclosed herein offers substantial advantages over the prior art. As discussed earlier the IVC graft disclosed by Desai et al. has a cylindrical framework, wherein a triangular prismatic insert is placed inside the cylindrical framework. The insert is placed in a manner that an edge of the prism faces the IVC flow thereby bifurcating the IVC flow. However, such a configuration leads to the SVC flow to directly collide with a flat surface of the insert. This head on collision results in turbulence, power loss and the like. In contrast, the device 300 has a flow separator 308 that is configured to bifurcate both the SVC and IVC flow. The flow separator 308 has a superior portion 512 that traverses into the lumen of the SVC thereby bifurcating the SVC flow. Therefore, the uniform bifurcation of the IVC and SVC flow in the device 300 results in reduced turbulence, power loss so on and so forth.

Further, in the IVC graft disclosed by Desai et al. the insert is placed at the distal end of the uniformly cylindrical framework. Therefore, the insert constricts the path of flow of blood thereby resulting in an undesirable drop in pressure of the blood entering the PA's. The drop in the pressure of the blood in the PA's makes it harder for the blood from the PA's to enter the lungs. The device 300 has a diverging configuration from the first end 304 to the second end 306. This configuration provides a large passage for the flow of blood from the IVC into the PA's thereby eliminating the drop in pressure of the blood entering the lungs.

The U.S. Pat. No. 7,811,244 discloses an embodiment (Optiflo 200) of an extracardiac connection, wherein the connection has a cross shaped external framework. In the embodiment, a diamond shaped insert is placed inside the framework to separate the flow. The projection of the insert towards the IVC bifurcates the IVC flow and directs the flow to the PA's. However, the projection of the insert towards the SVC, does not bifurcate the flow from SVC, rather it is configured to address the problems associated with a small SVC that are not suitable for anastomosis. Unlike the extracardiac connection as disclosed in U.S. Pat. No. 7,811,244, the device 300 has a flow separator 308 that traverses into the lumen of the SVC to bifurcate the SVC flow. This bifurcation of both the SVC and IVC flow eliminates the turbulence at the junction of the bifurcated IVC and SVC flows thereby minimizing the energy loss.

Further, the embodiment (Optiflo 200) comprises a cross-shaped external framework that has four cylindrical ends. The cylindrical ends of the extracardiac connection are configured to be anastomosed to the IVC, SVC, right and left pulmonary arteries respectively. Therefore, the placement of an insert inside the framework constricts the path of flow of blood from IVC around the insert thereby resulting in a drop in pressure of blood entering the PA's. This particular disadvantage is overcome in the device 300 by the divergent funnel shaped configuration of the hollow body 302. The hollow body 302 diverges from the first end 304 towards the second end 306 thereby increasing the space available between the flow separator 308 and lateral side of the hollow body 302. Therefore, the blood flows through a larger passage and thus eliminating any undesirable pressure drop in the blood entering the PA's.

Additionally, the cross shaped external framework results in an increase in the number of suture lines (quadruple anastomosis) and excessive removal of native tissue. The more the number of suture lines, the complex the surgical process. The device 300 requires only one (wire-reinforced first end)/two suture lines to be affixed to the heart.

The device 300, wherein the first end 304 is wire reinforced facilitates a transatrial placement of the first end 304 within the lumen of the IVC. Thus, the need for a separate IVC anastomosis is eliminated. Therefore, effectively the device 300 requires only one suture line (between the second end and PA) to be affixed to the heart. Therefore, the surgical process performed in affixing the device 300 is simpler than that of prior art.

The surgical procedure of deploying the Optiflo not only necessitates a quadruple anastomosis but also mandates the take down of the Glenn shunt (SVC to PA) performed previously on the patient. In contrast, the deployment of the device 300 does not require take down of the Glenn shunt.

The inferior portion 410 of the flow separator 308 that can be offset with respect to the longitudinal axis 514 of the hollow body 302 enables increased blood flow to a particular lung. Such a configuration enables increased blood flow to a lung that has higher PVR in an unbalanced PVR. There is no prior art that discloses such an extracardiac connection configuration.

The device 300 enables an equal distribution of hepatic blood to both lungs (even in cases of unbalanced PVR), thereby preventing the PAVM formation that is a prevalent among patients who have undergone cavopulmonary anastomosis.

The processes described above are described as a sequence of steps; this was done solely for the sake of illustration. Accordingly, it is contemplated that some steps may be added, some steps may be omitted, the order of the steps may be re-arranged, or some steps may be performed simultaneously.

Although embodiments have been described with reference to specific example embodiments, it will be evident that various modifications and changes may be made to these embodiments without departing from the broader spirit and scope of the system and method described herein. Accordingly, the specification and drawings are to be regarded in an illustrative rather than a restrictive sense.

Many alterations and modifications of the present invention will no doubt become apparent to a person of ordinary skill in the art after having read the foregoing description. It is to be understood that the phraseology or terminology employed herein is for the purpose of description and not of limitation. It is to be understood that the description above contains many specifications, these should not be construed as limiting the scope of the invention but as merely providing illustrations of some of the personally preferred embodiments of this invention.

What is claimed is:

1. A device (300) for use in total cavopulmonary connection, the device (300) comprising:
    a hollow body (302) comprising:
        a first end (304) configured to receive blood from inferior vena cava; and
        a second end (306) configured to be connected to pulmonary artery; and
    a flow separator (308) for guiding blood from inferior vena cava and superior vena cava to right pulmonary artery and left pulmonary artery, the flow separator (308) comprising an inferior end (402), a centre piece (414) and a superior end (404), wherein,
        the inferior end (402) is between the first end (304) and the second end (306) of the hollow body (302);
        the flow separator (308) is dimensioned to have the superior end (404) enter superior vena cava when the second end (306) is connected to the pulmonary artery; and
        the centre piece (414) defines a first pair of concave channels (406a and 406b) converging to define an inferior portion (410), wherein the pair of concave channels (406a and 406b) are configured to interface with blood from inferior vena cava and guide the blood from inferior vena cava to right pulmonary artery and left pulmonary artery.

2. The device (300) as claimed in claim 1, wherein the second end (306) is of elliptical cross-section.

3. The device (300) as claimed in claim 2, wherein dimension of the major axis of the second end (306) is greater than dimension of the first end (304) along a lateral axis of the first end (304).

4. The device (300) as claimed in claim 3, wherein ratio between the dimension of the major axis of the second end (306) and the dimension of the first end (304) along the lateral axis is in the range of 1.72 to 2.33.

5. The device (300) as claimed in claim 4, wherein the dimension of the major axis of the second end (306) is in the range of 38 mm to 42 mm.

6. The device (300) as claimed in claim 5, wherein the dimension of the first end (304) along the lateral axis is in the range of 18 mm to 22 mm.

7. The device (300) as claimed in claim 6, wherein the distance between the first end (304) and the second end (306) is in the range of 70 mm to 90 mm.

8. The device (300) as claimed in claim 1, wherein the hollow body (302) diverges from the first end (304) towards the second end (306) to define a smooth curvature.

9. The device as claimed in claim 1, wherein,
    the first end (304) is of circular cross-section;
    the second end (306) is of elliptical cross-section; and
    the hollow body (302) diverges from the first end (304) towards the second end (306) to define a smooth curvature.

10. The device (600) as claimed in claim 1, wherein the first end (304) of the hollow body (302) comprises a wire reinforcement (602).

11. The device (300) as claimed in claim 1, wherein the centre piece (414) defines a second pair of concave channels (408a and 408b), wherein the second pair of concave channels (408a and 408b) adjoins the first pair of concave channels (406a and 406b) to define a pair of lateral projections (412a and 412b) that extend into the lumen of pulmonary artery, wherein the second pair of concave channels (408a and 408b) are configured to face blood from superior vena cava.

12. The device (300) as claimed in claim 1, wherein,
the flow separator (308) comprises a superior portion (512), which ends at the superior end (404);
the superior end (404) is tapered and defines a wedge;
the superior portion (512) is configured to be housed within the superior vena cava (502) when the second end (306) is connected to the pulmonary artery; and
the superior portion (512) is configured to interface with blood from superior vena cava (502) and guide the blood from superior vena cava (502) to right pulmonary artery (506) and left pulmonary artery (504).

13. The device (300) as claimed in claim 12, wherein length of the superior portion (512) is in the range of 20 mm to 30 mm.

14. The device (300) as claimed in claim 12, wherein,
the superior portion (512) is cantilevered from the hollow body (302); and
the superior portion (512) is exposed in all directions before the device (300) is used in total cavopulmonary connection.

15. The device (800) as claimed in claim 1, wherein a portion of the first end (304) of the hollow body (302) is folded and a tear seam (804) is formed in the folded portion (802) of the first end (304) of the hollow body (302).

16. The device (800) as claimed in claim 15, wherein the tear seam (804) ruptures on application of force and expands the first end (304) of the hollow body (306).

17. The device (300) as claimed in claim 1, wherein a surface of the hollow body (302) defines a fenestration configured to be sutured to the wall of the right atrium.

18. The device (600) as claimed in claim 1, wherein a surface of the hollow body (302) comprises a plurality of ports (602) configured to provide access to one or more measurement device.

19. The device (300) as claimed in claim 1, wherein the inferior portion (410) of the flow separator (308), which is housed within the hollow body (302) is offset about a longitudinal axis of the hollow body (302).

* * * * *